(12) United States Patent
Halvorsen

(10) Patent No.: US 7,179,649 B2
(45) Date of Patent: *Feb. 20, 2007

(54) DIFFERENTIATION OF ADIPOSE STROMAL CELLS INTO OSTEOBLASTS AND USES THEREOF

(75) Inventor: Yuan-di C. Halvorsen, Holly Springs, NC (US)

(73) Assignee: Zen Bio, Inc., Research Triangle Park, NC (US)

( * ) Notice: Subject to any disclaimer, the term of this patent is extended or adjusted under 35 U.S.C. 154(b) by 864 days.

This patent is subject to a terminal disclaimer.

(21) Appl. No.: 10/061,214

(22) Filed: Mar. 14, 2002

(65) Prior Publication Data

US 2002/0119126 A1     Aug. 29, 2002

Related U.S. Application Data

(63) Continuation of application No. 09/554,868, filed on May 19, 2000, now Pat. No. 6,391,297.

(60) Provisional application No. 60/067,334, filed on Dec. 2, 1997.

(51) Int. Cl.
*C12N 5/00* (2006.01)

(52) U.S. Cl. .................. 435/366; 435/377; 435/325; 424/93.7; 424/93.21

(58) Field of Classification Search ................ 435/366, 435/377, 325; 424/93.7, 93.21
See application file for complete search history.

(56) References Cited

U.S. PATENT DOCUMENTS

| | | | |
|---|---|---|---|
| 5,226,914 A | 7/1993 | Caplan et al. | |
| 5,446,143 A | 8/1995 | Simpson et al. | |
| 5,486,359 A | 1/1996 | Caplan et al. | |
| 5,786,207 A | 7/1998 | Katz et al. | |
| 6,153,432 A | 11/2000 | Halvorsen et al. | |
| 6,200,606 B1 | 3/2001 | Peterson et al. | |
| 6,391,297 B1 * | 5/2002 | Halvorsen | 424/93.7 |
| 6,426,222 B1 | 7/2002 | Patat et al. | |
| 6,429,013 B1 * | 8/2002 | Halvorsen et al. | 435/377 |
| 6,555,374 B1 * | 4/2003 | Gimble et al. | 435/371 |
| 6,841,150 B2 * | 1/2005 | Halvorsen et al. | 424/93.7 |

FOREIGN PATENT DOCUMENTS

| WO | WO 99/28444 A1 | 6/1999 |
|---|---|---|
| WO | WO 00/44882 A2 | 8/2000 |
| WO | WO 00/53795 A1 | 9/2000 |
| WO | WO 01/62901 A1 | 8/2001 |

OTHER PUBLICATIONS

U.S. Appl. No. 60/123,711, filed Mar. 10, 1999, Katz et al.
U.S. Appl. No. 60/163,462, filed Oct. 29, 1999, Katz et al.
Ashton et al., "Formation of Bone and Cartilage by Marrow Stromal Cells in Diffusion Chambers *in Vivo*," *Clin Orthop*, (1980), vol. 151, pp. 294-307.
Becker et al., "Use of Recombinant Adenovirus of Metabolic Engineering of Mammalian Cells," *Meth Cell Biol*, (1994), vol. 43, pp. 161-189.
Benayahu et al., "Subpopulations of Marrow Stromal Cells Share a Variety of Osteoblastics Markers," *Calcif Tiss Int.*, (1991), vol. 49, pp. 202-207.
Bennett et al., "Adipocytic Cells cultured from Marrow Have Osteogenic Potential," *J Cell Sci*, (1991), vol. 99, pp. 131-136.
Beresford et al., "Evidence of An Inverse Relationship Between the Differentiation of Adipocytic and Osteogenic Cells in Rat Marrow Stromal Cell Cultures," *J Cell Sci*, (1992), vol. 102. pp. 341-351.
Boynton et al., "Human Osteoblasts Survive and Deposit New Bone When Human Bone is Implanted in SCID Mouse," *Bone*, (1996), vol. 18, pp. 321-326.
Celeste, "Identification of Transforming Growth Factor β Family Members Present in Bone-Inductive Protein Purified from Bovine Bone," *Proc Natl Acad Sci*, (1990), vol. 87, pp. 9843-9847.
Chen, "Bone Morphogenetic Protein-2b Stimulation of Growth and Osteogenic Phenotypes in Rat Osteoblast-Like Cells: Comparison with TGF-β," *J Bone Min Res*, (1991), vol. 6, pp. 1387-1393.

(Continued)

*Primary Examiner*—L Blaine Lankford
(74) *Attorney, Agent, or Firm*—Drinker Biddle & Reath LLP

(57) ABSTRACT

The invention provides methods and compositions for differentiating stromal cells from adipose tissue into cells having osteoblastic properties, and methods for improving a subject's bone structure. The methods comprise culturing stromal cells from adipose tissue in β-glycerophosphate and ascorbic acid and/or ascorbate-2-phosphate for a time sufficient to allow differentiation of said cells into osteoblasts. Such methods and compositions are useful in the production of osteoblasts for autologous transplantation into bone at a surgical site or injury. The compositions comprise adipose stromal cells, a medium capable of supporting the growth of fibroblasts and amounts of β-(glycerophosphate and ascorbic acid and/or ascorbic-2 phosphate sufficient to induce the differentiation of said stromal cells into osteoblasts.

The invention further provides methods of identifying compounds that affect osteoblast differentiation. Such compounds are useful in the study of bone development and in the treatment of bone disorders, including bone fractures and osteoporosis.

1 Claim, 6 Drawing Sheets

OTHER PUBLICATIONS

Connolly, "Injectable Bone Marrow Preparations to Stimulate Osteogenic Repair," *Clin Orthop*, (1995), vol. 313, pp. 8-18.

Cook et al., "Osteogenic Protein-1," *Clin Orthop*, (1996), vol. 324, pp. 29-38.

Cook et al., "Evaluation of Hydroxylapatite Graft Materials in Canine Cervical Spine Fusions," *Spine*, (1986), vol. 11, pp. 305-309.

Dorheim et al., "Osteoblastic Gene Expression During Adipogenesis in Hematopoietic Supporting Murine Bone Marrow Stromal Cells," *J Cell Physiol*, (1993), vol. 154, pp. 317-328.

Gimble et al., "The Function of Adipocytes in the Bone Marrow Stroma: An Update," *Bone*, (1996), vol. 19, pp. 421-428.

Gimble et al., "Adipogenesis in a Myeloid Supporting Bone Marrow Stromal Cell Line," *J Cell Biochem.* (1992), vol. 50, pp. 73-82.

Gimble et al., "Adipogenesis in a Murine Bone Marrow Stromal Cell Line Capable of Supporting β Lineage Lymphocyte Growth and Proliferation: Biochemical and Molecular Characterization," *Eur J Immunol.* (1990), vol. 20, pp. 379-387.

Grigoriadis et al., "Differentiation of Muscle, Fat, Cartilage, and Bone from Progenitor Cells Present in a Bone-Derived Clonal Cell Population: Effect of Dexamethasone," *J Cell Biol*, (1988), vol. 106, pp. 2139-2151.

Gundle et al., "Human Bone Tissue Formation in Diffusion Chamber Culture in Vivo by Bone-Derived Cells and Marrow Stromal Fibroblastic Cells," *Bone*, (1995) vol. 16, pp. 597-601.

Hauner et al., "Promoting Effect of Glucocorticoids on the Differentiation of Human Adipocyte Precursor Cells Cultured in a Chemically Defined Medium," *J Clin Invest*, (1989), vol. 84, pp. 1663-1670.

Haynesworth et al., "Characterization of Cells with Osteogenic Potential from Human Marrow," *Bone*, (1992), vol. 13, pp. 81-88.

Herron et al., "The Failure of Ethylene Oxide Gas-Sterilized Freeze-Dried Bone Graft for Thoracic and Lumbar Spinal Fusion," *Spine*, (1989), vol. 14, pp. 496-500.

Kaban et al., "Treatment of Jaw Defects with Demineralized Bone Implants," *J Oral Maxillofac Surg*, (1982), vol. 40, pp. 623-626.

Kale et al., "Osteoinductive Agents," *Am J Orthop*, (1995) vol. 24, pp. 752-761.

Kaplan et al., "Clinical Vignette Fibrodysplasia Ossificans Progressiva (FOP)," *J Bone Min Res*, (1997), vol. 12, p. 855.

Katzer, "Histopathology of Rare Chondroosteoblastic Metaplasia in Benign Lipomas," *Path Res Proct*, (1989), vol. 184, pp. 437-443.

Krebsbach et al., "Bone Formation In Vivo: Comparison of Osteogenesis by Transplanted Mouse and Human Marrow Stromal Fibroblasts," *Transplantation*, (1997), vol. 63, pp. 1059-1069.

Kurz et al., "Harvesting Autogenous Iliac Bone Grafts: A Review of Complications and Techniques," *Spine*, (1989), vol. 14, pp. 1324-1331.

Kuznetsov et al., "Single-Colony Derived Strains of Human Marrow Stromal Fibroblasts from Bone After Transplantation In Vivo," *J Bone Min Res*, vol. 12, pp. 1335-1347.

Lane, "Current Approaches to Experimental Bone Grafting," *Ortho Clin N Amer*, (1987), vol. 18, pp. 213-225.

Laurie et al., "Donor-Site Morbidity after Harvesting Rib and Iliac Bone," *Plas Rec Surg*, (1984), vol. 73, pp. 933-938.

Meunier-Durmort et al., "Efficient Transfer of Regulated Genes in Adiopocytes and Hepatoma Cells by the Combination of Liposomes and Replication-Deficient Adenovirus," *Eur. Biochem.*, (1996), vol. 237., pp. 660-667.

Mulliken et al., "Use of Demineralized Allogeneic Bone Implants for the Correction of Maxillocraniofacial Deformities," *Ann Surg*, (1981), vol. 194, pp. 366-372.

Parfitt, "The Two-Stage Concept of Bone Loss Revisited," *Triangle*, (1992), vol. 31, pp. 99-110.

Sampath, "Recombinant Human Osteogenic Protein-1 (hOP-1) Induces New Bone Formation *in Vivo* with a Specific Activity Comparable with Natural Bovine Osteogenic Protein and Stimulates Osteoblast Proliferation and Differentiation *in Vivo*," *J Biol Chem*, (1992), vol. 267, ppl 20352-20362.

Shafritz et al., "Overexpression of an Osteogenic Morphogen in Fibrodysplasia Ossificans Progressiva," *N Engl J Med*, (1996), vol. 335, pp. 555-561.

Shima et al., "Anterior Cervical Discectomy and Interbody Fusion: An Experimental Study Using a Synthetic Tricalcium Phosphate," *J Neurosurg*, (1979), vol. 51, pp. 533-538.

Sonis et al., "Clinical Trial of Demineralized Bone Powder in the Treatment of Periodontal Defects," *J Oral Med*, (1983), vol. 3, pp. 117-122.

Stein et al., "Relationship of Cell Growth to the Regulation of Tissue-Specific Gene Expression During Osteoblast Differentiation," *FASEB J*, (1990), vol. 4, pp. 3111-3123.

Summers et al., "Donor Site Pain from the Ilium," *J Bone Joint Surg*, (1989), vol. 71B, pp. 677-680.

Takuwa, "Bone Morphogenetic Protein-2 Stimulates Alkaline Phosphatase Activity and Collagen Synthesis in Cultured Osteoblastic Cells, MC3T3-E1," *Biochem Biophys Res Com*, (1991), vol. 174, pp. 96-101.

Turner et al., "Patient Outcomes after Lumbar Spinal Fusions," *JAMA*, (1992), vol. 268, pp. 907-911.

Urist, "Bone: Formation by Autoinduction," *Science*, (1965), vol. 150, pp. 893-899.

Whitehill et al., "The Evolution of Stability in Cervical Spinal Constructs Using Either Autogenous Bone Graft or Methylmethacrylate Cement: A follow-Up Report on a Canine *In Vivo* Model," *Spine*, (1985), vol. 10, pp. 32-41.

Wozney et al., "Novel Regulators of Bone Formation: Molecular Clones and Activities," *Science*, (1988), vol. 242, pp. 1528-1534.

Yamaguchi et al., "Clonal Osteogenic Cell Lines Express Myogenic and Adipocytic Developmental Potential," *Calcif Tissue Int*, (1991), vol. 49, pp. 221-225.

Younger et al., "Morbidity at Bone Graft Donor Sites," *J Orthop Trauma*, (1989), vol. 3, pp. 192-195.

A. Poliard et al., 1995, The Journal of Cell Biology 130(6):1461-1472.

Mikos et al. 1997, J. Biomed. Mater. Res. 36:17-28.

Lecoeur et al. 1997, Biomaterials 18:989-993.

* cited by examiner

Osteoblasts (20X)

Adipocytes (20X)

- 20 days in culture
- Oil red O stained

Adipocytes (20X)
Osteoblasts (20X)

- 20 days in culture
- von Kassa stained

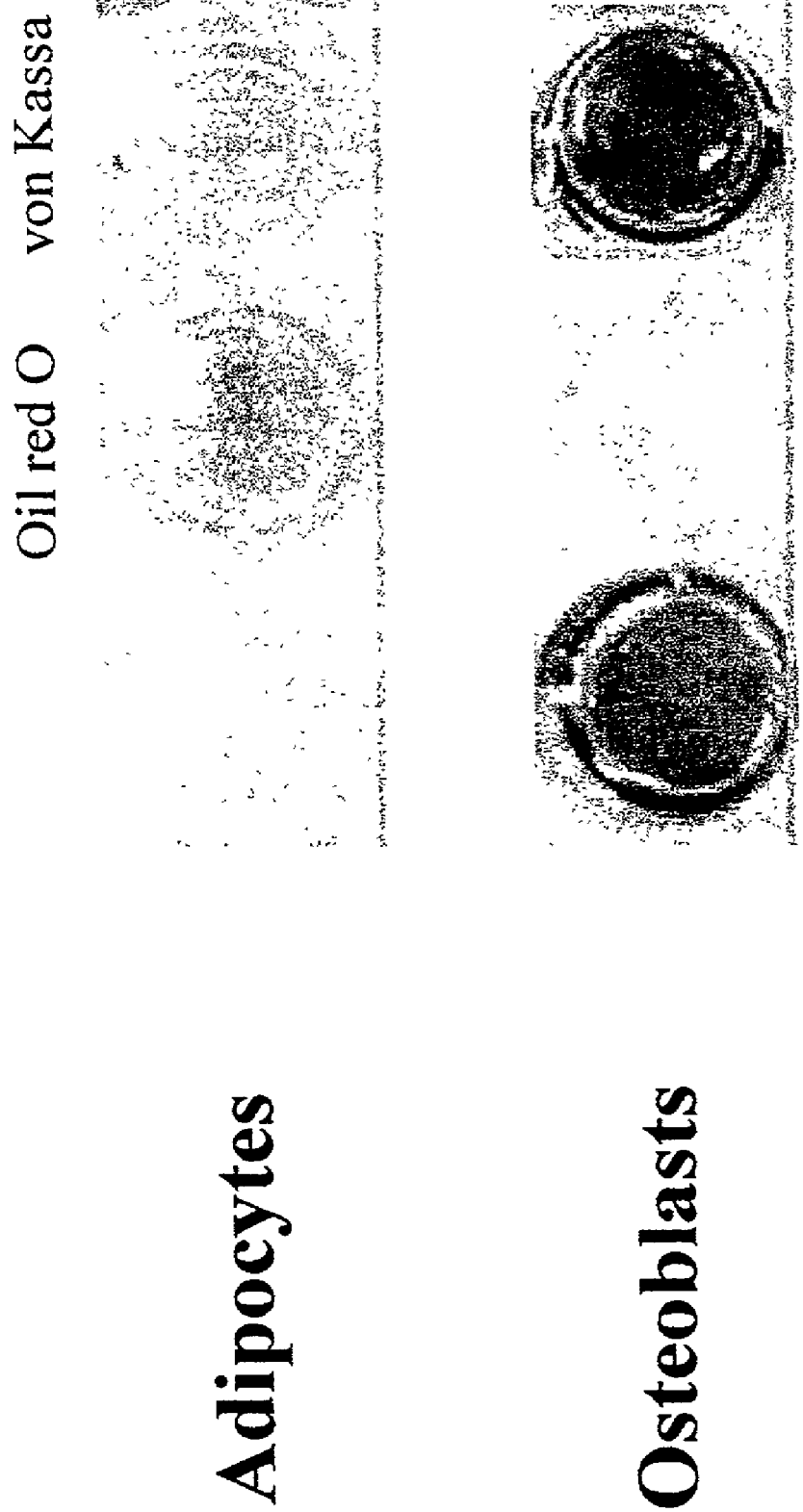

DIFFERENTIATION OF ADIPOSE STROMAL CELLS INTO OSTEOBLASTS AND USES THEREOF

This application is a CON of Ser. No. 09/554,868, filed May 19, 2000, now U.S. Pat. No. 6,391,297 which claims benefit under 35 USC 119(e) to Ser. No. 60/067,334, filed Dec. 2, 1997.

FIELD OF THE INVENTION

This invention relates to methods and compositions for the differentiation of stromal cells from adipose tissue into osteoblasts, and uses thereof.

BACKGROUND OF THE INVENTION

Osteoporosis is responsible for about 1.5 million fractures each year in the United States, of which about 300,000 are hip fractures. Fifty to 75% of patients with hip fractures are unable to live independently, resulting in increased costs of care. Osteoporosis is characterized by a greater than normal loss of bone density as people age. This disease occurs with a high frequency (>30% of females over age 60) in Western and Asian cultures, and is increasing in prevalence as longevity increases. While the exact cause of these bone repair disorders is unknown, it is clear the dynamic process of bone remodeling is disrupted in a process characterized by a decrease in osteoblastic (bone-producing cells) activity and an increase in osteoclastic (bone degrading cells) activity (Parfitt (1992) *Triangle* 31:99–110; Parfitt (1992) In *Bone*, volume 1, B. K. Hall, ed. Teleford Press and CRC Press, Boca Raton, Fla., p. 351–429).

The use of bone grafts is conventional practice in orthopedics, neurosurgery and dentistry, as well as in plastic/reconstruction surgery and this utilization has been growing in frequency over the past two decades. With the exception of blood, bone is the most frequently transplanted tissue with an estimated 500,000 bone grafts used in the US annually. Common orthopedic uses of bone grafts include the management of non-unions and acute long bone fracture, joint reconstruction and to facilitate fusion of vertebral motion segments in treating a variety of spinal disorders (Lane (1987) *Ortho Clin N Amer* 18:213–225).

Currently, the most clinically acceptable grafting material is autologous bone. So-called autografts are often obtained from a secondary operative site. There are significant issues associated with autografts. These include lack of an adequate supply for large wounds or defects. Elderly individuals with osteoporosis or osteopenia make the use of an autograft problematic. The secondary morbidity associated with the harvesting operation is high. These complications include infections, pelvic instability (the bone is often harvested from the iliac crest), hematoma, and pelvic fracture (Laurie et al. (1984) *Plas Rec Surg* 73:933–938; Summers et al. (1989) *J Bone Joint Surg* 71B:677–680; Younger et al. (1989) *J Orthop Trauma.* 3:192–195; Kurz et al. (1989) *Spine* 14:1324–1331). In addition, chronic pain at the donor site is the second most frequently reported complication (Turner et al. (1992) *JAMA* 268:907–911). Finally, the ability to shape the autograft to the defect/wound site is limited due to the rigid nature of the material.

Recent investigations have focused on the use of a variety of matrices, either inorganic such as hydroxyapatite (Flatley et al. (1983) *Clin Orthop Rel Res* 179:246–252; Shima et al. (1979) *J Neurosurg* 51:533–538; Whitehill et al. (1985) *Spine* 10:32–41; Herron, et al. (1989) *Spine* 14:496–500; Cook et al. (1986) *Spine* 11:305–309; the contents of which are incorporated herein by reference) or organic such as demineralized bone matrix (DBM) (reviewed in Ashay et al. (1995) *Am J Orthop* 24:752–761; the contents of which are incorporated herein by reference). These matrices are thought to be osteoconductive (facilitate the invasion of bone forming cells in an inert matrix) or osteoinductive (induce the transformation of recruited precursor cells to osteoblasts). A number of successful clinical outcomes have been observed with some of these products approved for use clinically by the Food and Drug Administration. In spite of these successes, a number of issues remain for the utility of these matrices. The first is the variable subject response to DBM. Also these matrices take much longer than autologous bone transplantation to develop significant structural integrity and bear load effectively.

An alternative to transplantation and the use of simple matrices is the admixture of bone marrow or bone marrow stromal cells with DBM. Ideally the cells and DBM will be derived from the same subject although allogeneic DBM has already been used clinically with initial success (Mulliken et al. (1981) *Ann Surg* 194:366–372; Kaban et al. (1982) *J Oral Maxillofac Surg* 40:623–626). Transplantation methods using autologous bone marrow cells with allogeneic DBM have yielded good results (Connolly (1995) *Clin Orthop* 313:8–18). However, issues that may impact the widespread use of these techniques include potential for contamination by non-self materials, the acceptability of the patient for donating bone marrow, and the potential complications that arise from bone marrow aspirations and depletion of bone marrow from the source.

A number of groups have shown that bone marrow stromal cells and cell lines derived thereof are capable of differentiating into cells biochemically and morphologically similar to osteoblasts (Dorheim et al. (1993) *J Cell Physiol* 154:317–328; Grigoriadis et al. (1988) *J Cell Biol* 106:2139–2151; Benayahu et al. (1991) *Calcif Tiss Int.* 49:202–207; the contents of which are incorporated by reference). In most cases, fibroblast-like cells were isolated from human or animal bone marrow and plated onto standard tissue cultureware. Generally, a standard media formulation, such as Dulbecco's Modified Eagle's Medium (DMEM) plus fetal calf serum 10–20% and antibiotics is used to select for the enrichment of these cells (Ashton et al. (1980) *Clin Orthop* 151:294–307; Sonis et al. (1983) *J Oral Med* 3:117–120). Cells were then stimulated to differentiate into osteoblasts by changing the medium to one containing 5–20% fetal calf serum, 2–20 mM β-glycerophosphate and 20–75 µM ascorbic acid or ascorbic-2-phosphate (Asahina et al. (1996) *Exp Cell Res* 222:38–47; Yamaguchi et al. (1991) *Calcif Tissue Int* 49:221–225; the contents of which are incorporated herein by reference). After 14–21 days in culture, many of these cell types and cell lines will mineralized matrices on the cultureware as evidenced by positive von Kossa staining. Other phenotypic indicators of osteoblast lineage include elevated secreted alkaline phosphatase activity; the presence of secreted osteocalcin in the media; and the increased expression of several genes thought to be specifically expressed in osteoblasts, including osteocalcin, osteopontin, and bone sialoprotein (Stein et al. (1990) *FASEB J* 4:3111–3123; Dorheim et al. (1993) *J Cell Physiol* 154:317–328; Asahina et al. (1996) *Exp Cell Res* 222:38–47; Yamaguchi et al. (1991) *Calcif Tissue Int* 49:221–225).

There have been a number of detailed studies carried out in several laboratories demonstrating that transplanted bone marrow stromal cells can form ectopic bone (Gundle et al. (1995) *Bone* 16:597–603; Haynesworth et al. (1992) *Bone*

13:81–89; Boynton et al. (1996) *Bone* 18:321–329). For example, human and murine bone marrow stromal fibroblasts have been transplanted into immunodeficient SCID mice (Krebsbach et al. (1997) *Transplantation* 63:1059–1069; Kuznetsov et al. (1997) *J Bone Min Res* 12:1335–1347). Using antibody and histochemical markers, it was demonstrated that the donor bone marrow stromal cells account for the newly developed osteoblasts at sites of ectopic bone formation in the presence of an inductive matrix. Murine cells formed bone in the presence of hydroxyapatite/tricalcium phosphate particles (HA/TCP), gelatin, poly-L-lysine, and collagen. In contrast, human stromal cells efficiently formed bone only in the presence HA/TCP. No exogenous BMP was required in these studies.

Bone formation is not limited to the skeleton. For example, the introduction of ceramic or demineralized bone matrix into intramuscular, subrenal capsular or subcutaneous sites will result in bone formation if the area is simultaneously expressing bone morphogenetic protein (Urist (1965) *Science* 150:893–899). These results suggest that cells present in these tissues have some capability of forming bone precursor cells under the proper environmental conditions.

Ectopic bone formation in soft tissue such as fat is a rare pathologic condition observed in patients with fibrosis ossificans progressiva, an inherited disease. While the etiology of the disease is not completely understood, it arises in part from the abnormal expression of BMP by lymphocytes localized to sites of soft tissue injury (Kaplan et al. (1997) *J Bone Min Res* 12:855; Shafritz et al. (1996) *N Engl J Med* 335:555–561]). Bone formation is also observed on rare occasions in lipomas (Katzer (1989) *Path Res Pract* 184: 437–443).

The stromal-vascular fraction isolated from adipose tissue after collagenase treatment has been demonstrated to contain a large quantity of preadipocytes, or cells that are predisposed to differentiate into adipocytes (Hauner et al. (1989) *J Clin Invest* 34:1663–1670). These cells can spontaneously differentiate into adipocytes at relatively low frequency or respond to adipogenic agonists such as thiazolidinediones to a much higher frequency of differentiation (Halvorsen (1997) *Strategies* 11:58–60; Digby (1997) *Diabetes* 4:138–141). There is evidence to suggest that stromal cells exhibit a reciprocal pattern of differentiation between these lineages (Gimble et al. (1996) *Bone* 19:421–428; Bennett et al. (1991) *J Cell Sci* 99:131–139; Beresford et al. (1992) *J Cell Sci* 102:341–351). Specifically, adipogenesis is accompanied by reduced osteoblastic potential while osteogenesis is accompanied by reduced adipogenic potential.

Under certain conditions, bone marrow stromal cells can be differentiated into adipocytes. In fact, several bone stromal cell lines have been extensively characterized with respect to this ability (Gimble et al. (1990) *Eur J Immunol* 20:379–387; Gimble et al. (1992) *J Cell Biochem* 50:73–82; Gimble et al. (1996) *Bone* 19:421–428). However, prior to the instant invention, it was not known that stromal cells isolated from adipose tissue could be made to differentiate into osteoblasts.

SUMMARY OF THE INVENTION

The invention provides methods and compositions for differentiating stromal cells from adipose tissue into cells having osteoblastic properties, and methods for improving a subject's bone structure. The methods comprise culturing stromal cells from adipose tissue in β-glycerophosphate and ascorbic acid and/or ascorbate-2-phosphate for a time sufficient to allow differentiation of said cells into osteoblasts. Such methods and compositions are useful in the production of osteoblasts for autologous transplantation into bone at a surgical site or injury. The compositions comprise adipose stromal cells, a medium capable of supporting the growth of fibroblasts and differentiation inducing amounts of β-glycerophosphate and ascorbic acid and/or ascorbic-2 phosphate.

The invention further provides methods of identifying compounds that affect osteoblast differentiation. Such compounds are useful in the study of bone development and in the treatment of bone disorders, including bone fractures and osteoporosis.

DETAILED DESCRIPTION OF THE INVENTION

Figure 1:
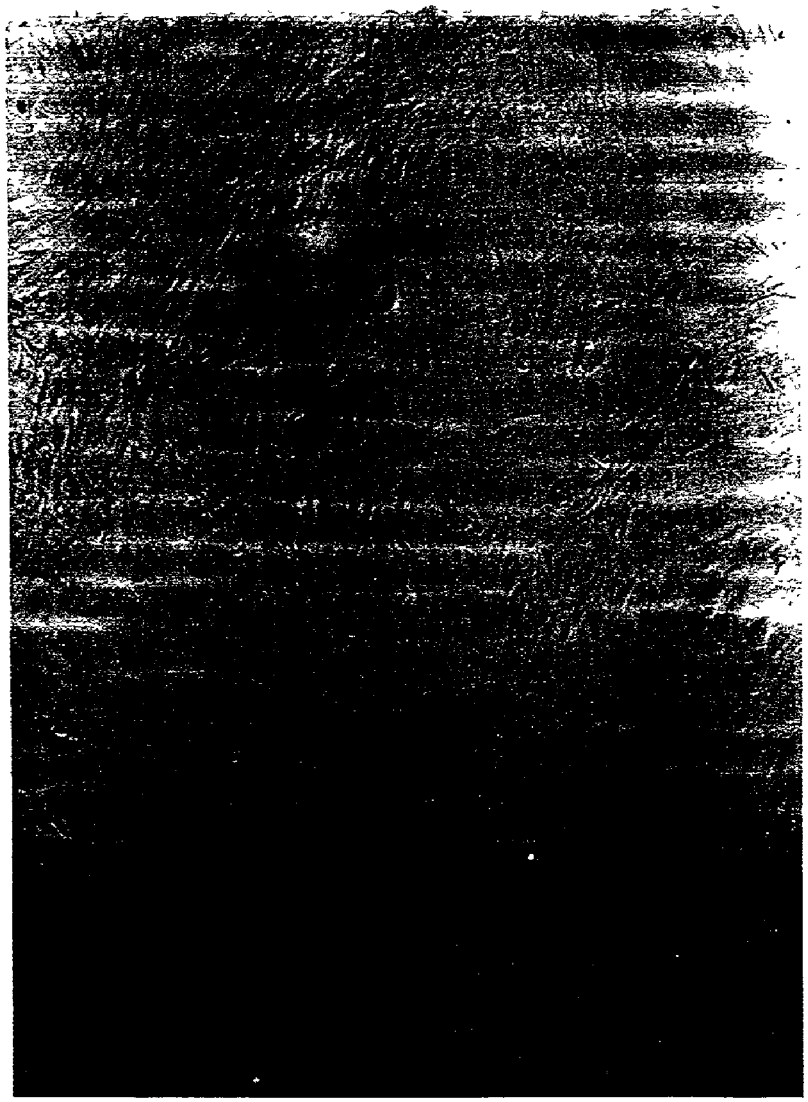
FIG. 1 shows the morphological changes that occur in human adipose stromal cells induced to differentiate into osteoblasts by treatment with osteoblast differentiation medium.

The present invention provides methods for differentiating adipose stromal cells into osteoblasts. The osteoblasts produced by the methods of the invention are useful in providing a source osteoblasts for research or transplantation into a subject's bone, at the site of surgery or fracture. Thus, in one aspect, the invention provides a method of differentiating adipose stromal cells into osteoblasts, comprising: culturing said cells in a composition which comprises a medium capable of supporting the growth of fibroblasts and differentiation inducing amounts of β-glycerophosphate and ascorbic acid and/or ascorbic-2 phosphate.

In another aspect, the invention provides compositions for the differentiation of adipose stromal cells into osteoblasts. Such compositions comprise: adipose stromal cells, a medium capable of supporting the growth of fibroblasts and amounts of β-glycerophosphate and ascorbic acid and/or ascorbic-2 phosphate sufficient to induce the differentiation of said stromal cells into osteoblasts.

"Adipose stromal cells" refers to stromal cells that originate from adipose tissue. By "adipose" is meant any fat tissue. The adipose tissue may be brown or white adipose tissue. Preferably, the adipose is subcutaneous white adipose tissue. Such cells may comprise a primary cell culture or an immortalized cell line. The adipose tissue may be from any organism having fat tissue. Preferably the adipose tissue is mammalian, most preferably the adipose tissue is human. A convenient source of human adipose tissue is from liposuction surgery, however, the source of adipose tissue or the method of isolation of adipose tissue is not critical to the invention. If osteoblasts are desired for autologous transplantation into a subject, the adipose tissue will be isolated from that subject.

"Differentiation inducing amounts of β-glycerophosphate and ascorbic acid and/or ascorbic-2 phosphate" refers to concentrations of β-glycerophosphate and (ascorbic acid and/or ascorbic-2 phosphate), that when supplied in a medium capable of supporting the growth of fibroblasts (e.g., NIH-3T3 cells, human adipose stromal cells and the like), will induce the differentiation of said stromal cells into osteoblasts over a time period of about five days to eight weeks. Optimal concentrations and lengths of treatment may be determined by the practitioner through the use of known assays for differentiated osteoblasts. Such assays include, but are not limited to those that assess morphological or biochemical characteristics (e.g., secreted osteocalcin or other osteoblast-specific proteins or RNA).

The concentration of ascorbic acid and/or ascorbic-2-phosphate refers to any combined concentration of these compounds that total the stated concentration. For example, the definition of "50 µM ascorbic acid and/or ascorbic-2 phosphate" includes, but is not limited to, such permutations as: 50 µM ascorbic acid; 50 µM ascorbic-2 phosphate; 10 µM ascorbic acid and 40 µM ascorbic-2 phosphate; or 40 µM ascorbic acid and 10 µM ascorbic-2 phosphate.

Preferably the medium contains about 2–20 mM β-glycerophosphate and about 20–75 µM ascorbic acid and/or ascorbic-2 phosphate. More preferably, the medium contains about 5–15 mM β-glycerophosphate and about 40–60 mM ascorbic acid and/or ascorbic-2 phosphate. Most preferably, the medium contains about 10 mM β-glycerophosphate and about 50 µM ascorbic acid and/or ascorbic-2 phosphate.

Any medium capable a supporting fibroblasts in cell culture may be used. Media formulations that will support the growth of fibroblasts include, but are not limited to, Dulbecco's Modified Eagle's Medium (DMEM), alpha modified Minimum Essential Medium (αMEM), and Basal Medium Essential (BME) and the like. Typically, 5–20% Fetal Calf Serum (FCS) will be added to the above media in order to support the growth of fibroblasts. However, a defined medium could be used if the factors in FCS necessary for fibroblast growth were identified and provided in the growth medium.

Media useful in the methods of the invention may contain one or more compounds of interest, including, but not limited to, antibiotics, compounds that are osteoinductive, osteoconductive, or promote growth or differentiation, such as bone morphogenetic proteins or other growth factors. Examples of bone morphogenetic proteins include, but are not limited to, osteogenic protein-1, BMP-5, osteogenin, osteoinductive factor and bone morphogenetic protein-4 (Asahina et al. (1996) *Exp Cell Res* 222:38–47; Takuwa (1991) *Biochem Biophys Res Com* 174:96–101; Chen (1991) *J Bone Min Res* 6:1387–1390; Sampath (1992) *J Biol Chem* 267:20352–20362; Wozney et al. 1988 *Science* 242:1528–1534, the contents of which are incorporated herein by reference), and the like.

Preferably, the adipose tissue is treated so that the stromal cells are dissociated from each other and from other cell types, and precipitated blood components are removed. Typically, dissociation into single viable cells may be achieved by treating adipose tissue with proteolytic enzymes, such as collagenase and/or trypsin, and with agents that chelate $Ca^{2+}$. Stromal cells may then be partially or completely purified by a variety of means known to those skilled in the art, such as differential centrifugation, fluorescence-activated cell sorting, affinity chromatography, and the like. The partially or completely isolated stromal cells may then cultured in a media that will support the growth of fibroblasts for a period of between eight hours to up to five cell passages prior to treatment with media containing β-glycerophosphate and ascorbic acid and/or ascorbic-2-phosphate.

The stromal cells will be cultured in media containing β-glycerophosphate and ascorbic acid and/or ascorbic-2-phosphate for a time sufficient to induce differentiation into osteoblasts. The length of treatment with β-glycerophosphate and ascorbic acid and/or ascorbic-2-phosphate required for differentiation of stromal cells into osteoblasts is dependent upon a number of factors. Such factors include, but are not limited to, the concentrations of β-glycerophosphate and ascorbic acid and/or ascorbic-2-phosphate used, the medium used, the source of adipose tissue or stromal cells, the initial density of plating, the presence or absence of growth factors or bone morphogenetic proteins and the like. The concentration of β-glycerophosphate and ascorbic acid or ascorbic-2-phosphate and other conditions and factors may be optimized by the practitioner. Optimal concentrations and treatment times may be determined by measuring the percentage of cells that have differentiated into osteoblasts. This percentage may be monitored by morphological and biochemical assays and indices known to those skilled in the art. Such assays and indices include, but are not limited to, those that assess morphological or biochemical characteristics, such as the presence of calcium deposits or osteoblast-specific proteins or RNAs, von Kossa staining, osteocalcin secretion and alkaline phosphatase secretion.

Osteoblasts derived from adipose tissue stromal cells may be introduced into the bone of a human or animal subject at the site of surgery or fracture. Introduction of osteoblasts to bone is useful in the treatment of bone fractures and bone disorders, including osteoporosis. Thus, in another aspect, the invention is directed to a method of improving a subject's bone structure, comprising:

a) culturing stromal cells from adipose tissue in a composition which comprises a medium capable of supporting the growth of fibroblasts and differentiation inducing amounts of β-glycerophosphate and ascorbic acid and/or ascorbic-2 phosphate; and b) introducing said osteoblasts into a surgery or fracture site of said subject.

Preferably, the stromal cells are isolated from the adipose tissue of the subject into which the differentiated osteoblasts are to be introduced. However, the stromal cells may also be isolated from an organism of the same or different species as the subject. The subject may be any organism having bone tissue. Preferably the subject is mammalian, most preferably the subject is human.

The stromal cells or osteoblasts may be stably or transiently transformed with a nucleic acid of interest prior to introduction into a surgery or fracture site of the subject. Nucleic acid sequences of interest include, but are not limited to those encoding gene products that enhance the growth, differentiation and/or mineralization of osteoblasts. For example, an expression system for bone morphogenetic protein 4, can be introduced into the preadipocytes in a stable or transient fashion for the purpose of treating non-healing fractures or osteoporosis. Methods of transformation of stromal cells and osteoblasts are known to those skilled in the art, as are methods for introducing osteoblasts into a bone at the site of surgery or fracture.

The osteoblasts may be introduced alone or in admixture with a composition useful in the repair of bone wounds and defects. Such compositions include, but are not limited to bone morphogenetic proteins, hydroxyapatite/tricalcium phosphate particles (HA/TCP), gelatin, poly-L-lysine, and collagen. For example, osteoblasts differentiated from adipose stromal cells may be combined with DBM or other matrices to make the composite osteogenic (bone forming in it own right) as well as osteoinductive. Similar methods using autologous bone marrow cells with allogeneic DBM have yielded good results (Connolly (1995) *Clin Orthop* 313:8–18).

A further object of the invention is to provide methods for the identification and study of compounds that enhance the differentiation of stromal cells into osteoblasts. Compounds that enhance the differentiation of osteoblasts may play a role in the treatment of various bone disorders, including fractures and osteoporosis. In addition, compounds found to induce osteoblast differentiation are useful in for differentiating cells in vitro or in vivo. Conversely, compounds or factors found to block osteoblast differentiation may be useful in certain disease states where idiosyncratic bone production, such as Paget's disease or chondroosteoblastic metaplasia, may be treated by such compounds. Thus, in another aspect, the invention is directed to a method of identifying compounds that affect osteoblast differentiation, comprising:
a) culturing adipose stromal cells in the presence and absence of a compound to be tested for effect on osteoblast differentiation in a composition which comprises a medium capable of supporting the growth of fibroblasts and differentiation inducing amounts of β-glycerophosphate and ascorbic acid and/or ascorbic-2 phosphate; and
b) comparing osteoblast differentiation in said cells cultured in the presence of said compound to that of said cells cultured in the absence of said compound.

Any compound may be tested for its ability to affect the differentiation of stromal cells into osteoblasts. Appropriate vehicles compatible with the compound to be tested are known to those skilled in the art and may be found in the current edition of Remington's Pharmaceutical Sciences, the contents of which are incorporated herein by reference.

The results of the tests can be compared with results using known differentiation promoting agents, such as osteogenic protein 1 and bone morphogenetic protein-4 (Asahina et al. (1996) *Exp Cell Res* 222:38–47; Takawa (1991) supra; Chen (1991) supra; Sampath (1992) supra; Wozney et al. (1988) *Science* 242:1528–1534), which are known to promote differentiation of osteoblasts by increasing the expression of osteoblast markers such as osteocalcin, a definitive marker of osteoblast function (Celeste (1986) *Proc Natl Acad Sci* 87:9843–9872; Stein et al. (1990) *FASEB J* 4:3111–3123). Also, the results of such tests may be compared to known osteoblast differentiation inhibitors such as TNF-alpha, which results in complete or partial blocking of the conversion of stromal cells into osteoblasts.

The features and advantages of the present invention will be more clearly understood by reference to the following examples, which are not to be construed as limiting the invention.

EXAMPLES

Example I

Isolation of Stromal from Human Adipose Tissue

Human stromal cells were isolated from adipose tissue according to the procedures described by Rodbell (1964) *J Biol Chem* 239:375 and Hauner et al. (1989) *J Clin Invest* 84:1663–1670. Briefly, human adipose tissue from subcutaneous depots was removed by liposuction surgery. The adipose tissue was then transferred from the liposuction cup into a 500 ml sterile beaker and allowed to settle for about 10 minutes. Precipitated blood was removed by suction. A 125 ml volume (or less) of the tissue was transferred to a 250 ml centrifuge tube, and the tube was then filled with Krebs-Ringer Buffer. The tissue and buffer were allowed to settle for about three minutes or until a clear separation was achieved, and then the buffer was removed by aspiration. The tissue was washed with Krebs-Ringer Buffer an additional four to five times or until it was orange-yellow in color and the buffer was light tan in color.

The cells of the adipose tissue were dissociated by collagenase treatment. Briefly, the buffer was removed from the tissue and replaced with a 2 mg collagenase/ml Krebs Biffer (Worthington, Mass., USA, type I) solution at a ratio of 1 ml collagenase solution/ml tissue. The tubes were incubated in a 37° C. water bath with intermittent shaking for 30 to 35 minutes.

Stromal cells were isolated from other components of the adipose tissue by centrifugation for 5 minutes at 500 × g at room temperature. The oil and adipocyte layer was removed by aspiration. The remaining stromal-vascular fraction was resuspended in approximately 100 ml of phosphate buffered saline (PBS) by vigorous swirling, divided into 50 ml tubes and centrifuged for five minutes at 500×g. The buffer was carefully removed by aspiration, leaving the stromal cells. The stromal cells were then resuspended in stromal cell medium (DMEM (Morton (1970) *In Vitro* 6:89–108; Dulbecco (1959) *Virology* 8:396) /Ham's F-10 medium (Ham (1963) *Exp Cell Res* 29:515) (1:1, v/v); 10% (v/v) fetal calf serum; 15 mM HEPES, pH 7.4; 60 U/ml penicillin; 60 U/ml streptomycin; 15 µg/ml amphotericin B), plated at an appropriate cell density and incubated at 37° C. in 5% $CO_2$ overnight. Once attached to the tissue culture dish or flask, the cultured stromal cells may be used immediately or maintained in culture for up to 5 passages before being induced to differentiate into osteoblasts as described in Example 2 below.

Example 2

Differentiation of Extramedullary Adipose Stromal Cells into Osteoblasts

Adipose stromal cells were isolated as described in Example 1 and then treated as follows to induce differentiation into osteoblasts. Stromal cells were plated in 24-well and/or 6-well tissue culture plates in stromal cell medium (see above) at a density of about 22,000 cells/cm². After 24 hours, the stromal cell medium was replaced with osteoblast differentiation medium (DMEM with 10% fetal bovine serum (v/v); 10 mM β-glycerophosphate; 50 µg/ml ascorbate-2-phosphate; 60 U/ml penicillin; 60 U/ml streptomycin; 15 µg/ml amphotericin B). The osteoblast differentiation medium was replaced with fresh medium every 3 days for 3 weeks. When changing the media, one ml of conditioned media was collected and stored at −80° C. for later analysis of secreted factors. Alternatively, stromal cells isolated from adipose tissue were induced to differentiate into adipocytes according to the method of Hauner et al. (1989 J Clin Invest 34:1663–1670) by treatment with adipocyte differentiation medium.

Microscopic examination of cells treated with osteoblast medium as described above revealed morphological changes consistent with the appearance of osteoblasts (FIG. 1). After prolonged culture (21–28 days), several multi-cellular nodules formed in each culture well. The grainy appearance of the osteoblast culture, indicates the presence of calcium phosphate deposits and pre-bone structures. Because stromal cells isolated from adipose tissue also have the potential to differentiate into adipocytes when treated with an adipocyte differentiation medium, the cells treated with osteoblast medium were also examined for the presence of adipocytes. No obvious adipocytes in the cultures treated with osteoblast medium, as indicated by the lack of oil droplets appearing in the cytoplasm and lack of cells having the characteristic rounded adipocyte morphology.

Cells treated with the osteoblast differentiation medium were stained by the von Kossa method to determine whether the stromal cells had differentiated into osteoblasts. Briefly, fetal calf serum was serially diluted out of the medium by exchanging 80% of the medium several times with serum-free medium. The cells were fixed in 5% formaldehyde and then washed several times with PBS to remove any remaining serum. The fixed cells were incubated in 100% ethanol at 4° C. for about 10 minutes. The ethanol was then removed and the fixed cells were incubated in 0.5 ml 5% silver nitrate for 10 minutes under UV light at 254 nm. The cells were then rinsed 2–3 times in distilled water, incubated in 5% sodium thiosulfate for 5 minutes and then rinsed with water. The stained cells can be stored in 50% glycerol indefinitely. The results of von Kossa staining are shown in FIGS. 2B and 2C. Only cells receiving osteoblast medium stained positive and turned dark.

Oil Red O staining was performed as follows. Plates were rinsed with phosphate buffered saline several times to remove serum or bovine serum albumin in the culture medium. The cells were then fixed in methanol or 10% formaldehyde in phosphate buffered saline for 15 minutes to 24 hours. An Oil Red O working solution was prepared by adding 6 ml of a stock solution (0.5 g Oil Red O in 100 ml isopropanol) to 4 ml of $dH_2O$. The working solution was kept for an hour at room temperature before filtering through a Whatman #1 filter. Cells were stained with approximately 3 ml/100 mm plate or 1 ml/well in 6-well plate for 1 hour at room temperature and then rinsed several times with $H_2O$. All of the remaining wash water was removed. 150 µl/well isopropanol was added and the plate was incubated at room temperature for 10 minutes. The isopropanol was pipetted up and down several times, to ensure that all of the oil red O was in solution. The optical density was measured at 500 nM.

Figure 2A:
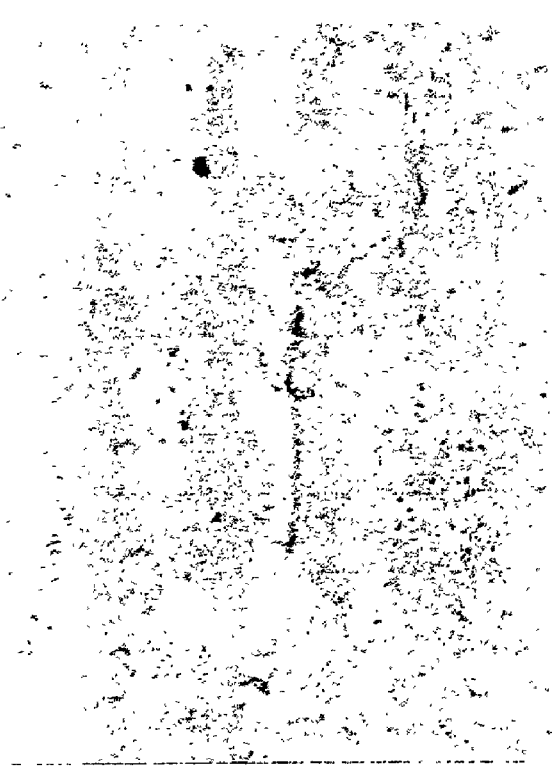
FIG. 2 shows adipose stromal cells that have been treated with osteoblast differentiation medium or adipocyte differentiation medium and stained with Oil Red O (FIGS. 2A and 2C) or by the von Kossa method (FIGS. 2B and 2C).
Figure 2A:
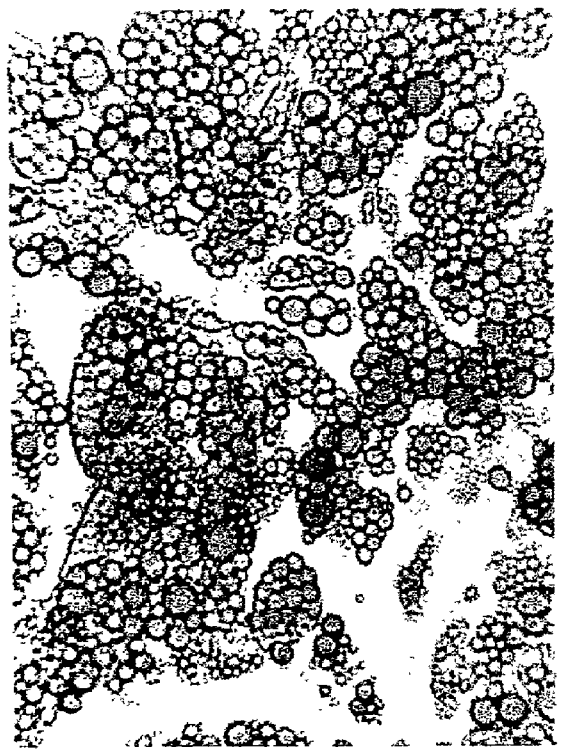
Figure 2B:
Figure 2B:
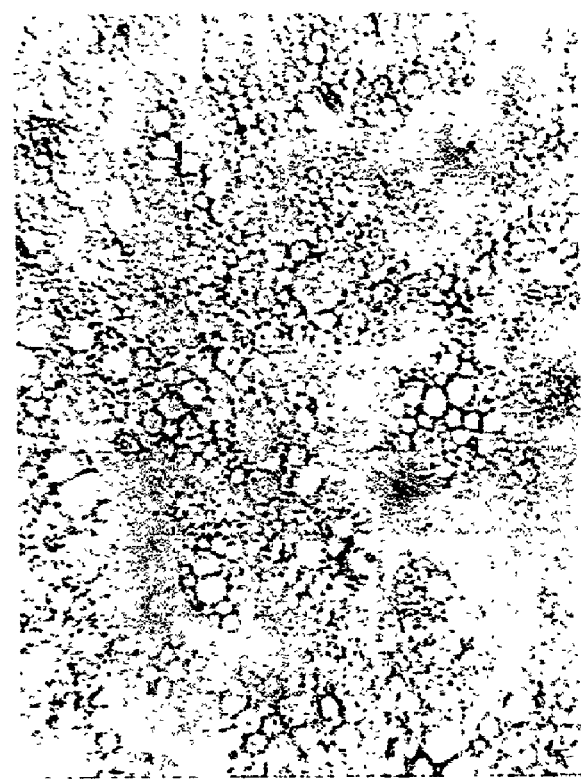

Cells receiving adipocyte differentiation medium stained with oil red O as described below displayed the characteristic red color indicating accumulation of lipid (FIG. 2A). Preadipocytes showed very small oil droplets accumulating after 4 weeks in culture. Cells receiving osteoblast medium showed some non-specific background oil red O, however, the staining was not associated with cells (FIG. 2C). These results suggest that stromal cells differentiating into osteoblasts do not have detectable adipocyte morphology. Lack of such neutral lipid accumulation is an indicator of loss of adipocyte function and lineage.

Figure 3:
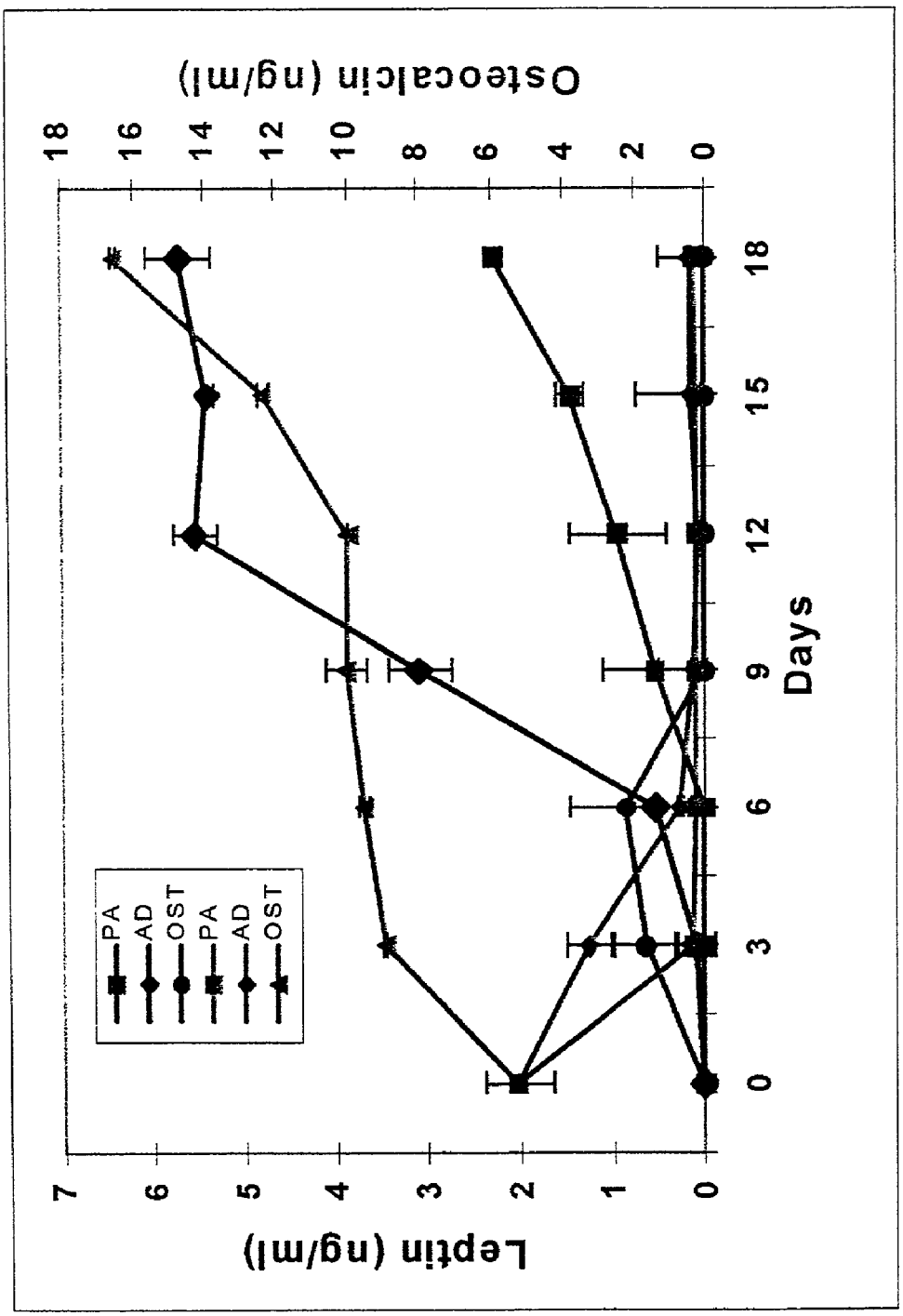
FIG. 3 shows the time course of concentrations of osteocalcin and leptin secreted into the media upon treatment of adipose stromal cells with stromal cell medium (PA), adipocyte medium (AD) or osteoblast medium (OST).

Biochemical changes indicative of osteoblast differentiation were also assessed. Osteocalcin is an osteoblast-specific secreted protein that can be measured by ELISA (Intact Human Osteocalcin K EIA kit, catalog number BT-460, Biomedical Technologies, Inc., Stoughton, Mass.). Media obtained from osteoblasts, preadipocytes, and adipocytes were examined for the presence of secreted osteocalcin. Briefly, conditioned medium (2 ml of medium from 40,000 cells after 72 hours) was collected and 20 µl of each medium was used for the assay. As shown in FIG. 3, there is increasing osteocalcin found in the media of the osteoblasts, while little or no osteocalcin secretion is seen in the adipose stromal cells and adipocytes.

Secreted leptin peptide was measured by a commercially available ELISA kit. Conditioned medium (2 ml of medium from 40,000 cells was conditioned for 72 hours) was collected and 100 µl of each medium was used for the assay following protocol suggested by the manufacturer. As expected, leptin is secreted into the media is increased during adipocyte differentiation but not in during osteoblast differentiation. The presence of leptin, an adipocyte-specific secreted protein, in the conditioned media is a clear marker for adipocyte activity. Osteoblasts and stromal cells fail to secrete any detectable leptin into the media, indicating a lack of adipocyte lineage, while only cells undergoing adipocyte differentiation secrete leptin after 2 weeks.

Figure 4:
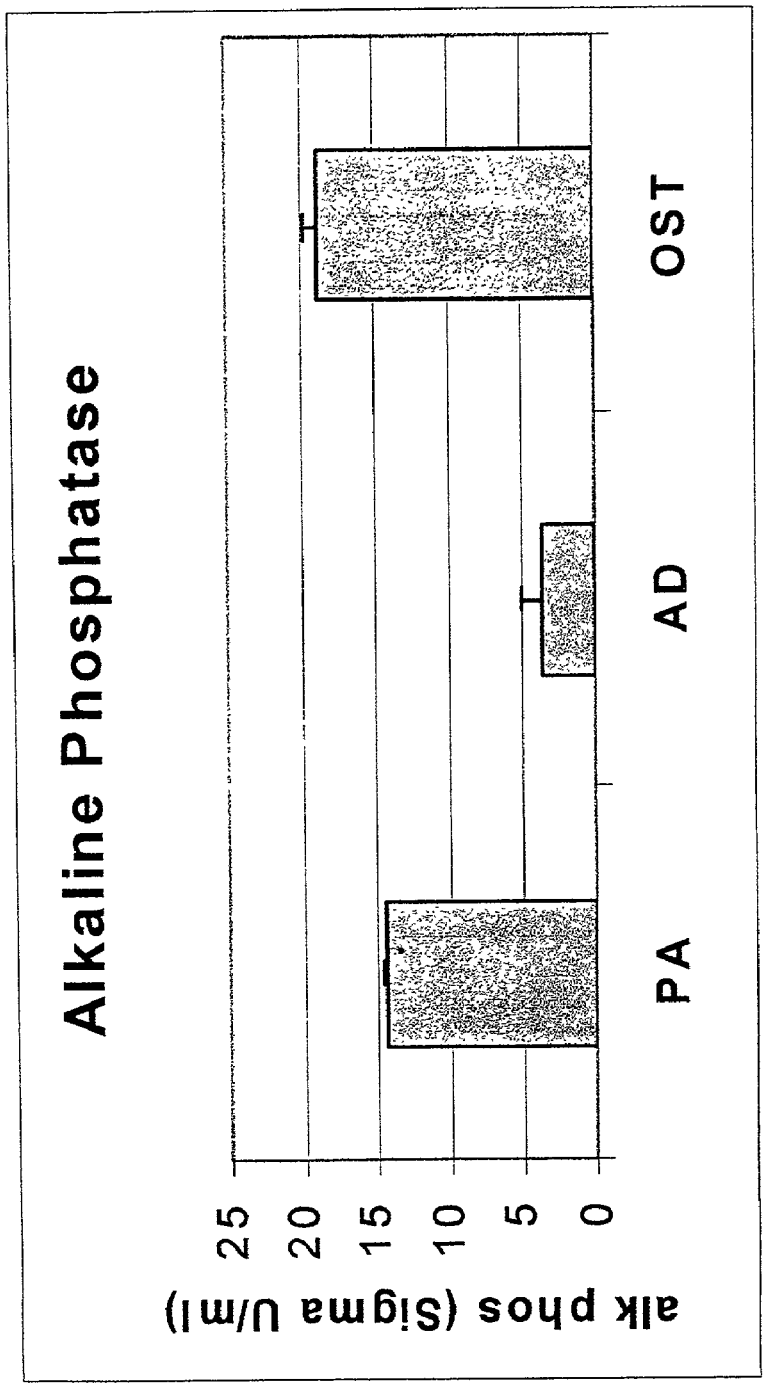
FIG. 4 shows the concentrations of alkaline phosphatase secreted by adipose stromal cells cultured for twenty-one days in stromal cell medium (SC), adipocyte differentiation medium (AD) or osteoblast differentiation medium (OST).

Another indicator of osteoblast lineage is the ability to secrete alkaline phosphatase. Cells were prepared and incubated as described above and the conditioned media assayed for alkaline phosphatase activity using a commercially available alkaline phosphatase assay kit (Sigma Diagnostic Inc., catalog number 104-LS, St Louis, Mo.). As shown in FIG. 4, the preadipocytes had a basal level of secreted alkaline phosphatase activity. Upon differentiation, the adipocytes lost this basal level of secreted activity while the osteoblasts showed an increase in the levels of alkaline phosphatase.

Example 3

Identification of Compounds Affecting Osteoblast Differentiation

Cultures of stromal cells isolated from adipose tissue according to the method described in Example 1 were used to study the effect compounds of interest on osteoblast differentiation. Osteoblasts were differentiated from adipose stromal cells as in Example 2, but in the presence and absence of a compound of interest. Differentiation was measured by assays for secreted osteocalcin. Compounds found to positively affect osteoblast differentiation using the method of this example include bone morphogenetic protein 4 and osteopontin-I (data not shown). These results are in agreement with the previous findings of Wozney et al. 1988 Science 242:1528–1534; Asahina et al. 1996 Exp Cell Res 222:38–47; and Cook et al. 1996 Clin Orthop. 324:29–38. Compounds that enhance osteoblast differentiation may be used to enhance the bone structure of a subject, as discussed below.

Example 4

Use of Osteoblasts in Bone Repair

Stromal cells are isolated from adipose tissue using liposuction from patients suffering from non-healing fractures or osteoporotic fractures using the method of Example 1. The preadipocytes are induced to differentiate to osteoblasts in vitro using the method described in Example 2. After 7–21 days, the differentiated osteoblasts are harvested, for example, by trypsin treatment or mechanical scraping of the differentiated cells from a tissue culture plate and then are concentrated by centrifugation at 3000×g for 10 min at 4–20° C. under sterile conditions. The harvested cells are resuspended in a collagen or Matrigel™ solution and are then injected directly into the fracture or surgery site using a 20 gauge or larger bore needle. Alternatively, before injection, the cells are mixed with DBM or a ceramic matrix such as ProOsteon 2000™ (Interpore Cross, Irvine, Calif.) or Collagraft™ (Zimmer Inc., Warsaw, Ind.). The amount of cells used will depend upon the surface area of the fracture and the nature of the fracture. Multiple treatments may be necessary depending upon the speed of recovery of the fracture desired. The result is decreased time to healing and increased bone density around the fracture site.

Example 5

Use of Genetically Altered Osteoblasts for Fractures or Osteoporosis

Stromal cells are isolated as described in Example 1 and genetic material (e.g., DNA encoding useful gene products, such as bone morphogenetic proteins, operably linked to a promoter) is introduced into the stromal cells using standard transfection methods such as calcium chloride (Maniatis et al. (1982) *Molecular Cloning: A Laboratory Manual,* Cold Spring Harbor Press, Cold Spring Harbor, N.Y.). Such a protocol has been developed using Effectene reagent and is described herein. In a microcentrifuge tube, 0.1–2.0 ug pCMV-βgal (Stratagene, Inc. La Jolla, Calif.) is added to 150 µl of Buffer EC (Qiagen Effectene™ kit; catalog number 301425, Qiagen Corp.). This allows the DNA to condense. 8 µl enhancer (Qiagen Effectene kit) is added to the condensed DNA. The tube containing the condensed DNA is then vortexed for one second and allowed to incubate at room temperature for 2–5 minutes. The tube is centrifuged briefly to remove drops at the top of the tube. 10 µl Effectene™ is added, the tube is vortexed for 10 seconds, and incubated at room temperature for 5–10 minutes. Following a 5–10 minute incubation time, 1 ml of medium is added to the DNA mixture.

120 µl of the old medium is removed from the cells and 70 µl of fresh medium is added. 25 µl of the DNA mixture is then to each well. The cells are incubated at 37° C. for about 5 hours. However, Effectene is not toxic and may be left on the cells for any period of time.

The cells are then rinsed once with 80 µl fresh medium and assayed at 72 hours post-infection for β-galactosidase activity using the method described by Maniatis et al. (1982). Such cells may be differentiated into osteoblasts under the methods described in Example I. Alternatively or the DNA maybe introduced directly into cells differentiated into osteoblasts.

Other methods of introducing nucleic acid sequences into cells may also be used. For example, adenovirus, may be used to introduce DNA into the stromal cells similarly to the protocols described by Becker et al. (1994) *Meth Cell Biol* 43:161–189 and Meunier-Durmont et al. (1996) *Eur Biochem* 237:660–667. The cells are then treated so they differentiate into osteoblasts as described above in Example I. Alternatively, the differentiated osteoblasts will be amenable to infection by viral particles. An addition of an antibiotic selection marker allows enrichment for cells bearing the introduced genetic material. The derived osteoblasts bearing the introduced genetic material are then introduced to fracture and osteoporotic bone marrow as described above in Example III.

All publications mentioned in the specification are indicative of the level of those skilled in the art to which this invention pertains. All publications are herein incorporated by reference to the same extent as if each individual publication was specifically and individually indicated to be incorporated by reference.

While the invention has been described with reference to specific embodiments, it will be appreciated that numerous variations, modifications, and embodiments are possible, and accordingly, all such variations, modifications, and embodiments are to be regarded as being within the spirit and scope of the invention.

The invention claimed is:

1. An isolated mammalian adipose tissue-derived stromal cell in combination with a substance that promotes differentiation to the osteoblast lineage, wherein said substance that promotes differentiation is selected from the group consisting of ascorbic acid, ascorbic 2-phosphate, bone morphogenetic proteins, β-glycerophosphate, or any combinations thereof.

* * * * *